US008044008B2

(12) United States Patent
Muzik et al.

(10) Patent No.: US 8,044,008 B2
(45) Date of Patent: Oct. 25, 2011

(54) DENTAL APPLIANCE CLEANSING COMPOSITION

(76) Inventors: Lynn Muzik, Los Gatos, CA (US); Nicholas Conley, Redwood, CA (US)

(*) Notice: Subject to any disclaimer, the term of this patent is extended or adjusted under 35 U.S.C. 154(b) by 27 days.

(21) Appl. No.: 12/189,160

(22) Filed: Aug. 10, 2008

(65) Prior Publication Data
US 2009/0042756 A1 Feb. 12, 2009

Related U.S. Application Data

(60) Provisional application No. 60/954,942, filed on Aug. 9, 2007.

(51) Int. Cl.
*C11D 3/20* (2006.01)
*C11D 3/00* (2006.01)
*C11D 3/48* (2006.01)
*C11D 17/00* (2006.01)

(52) U.S. Cl. ........ 510/161; 510/367; 510/370; 510/379; 510/382; 510/419

(58) Field of Classification Search .................. 510/161, 510/367, 370, 379, 382, 419
See application file for complete search history.

(56) References Cited

U.S. PATENT DOCUMENTS

| | | | |
|---|---|---|---|
| 2,409,718 A | 10/1946 | Snell | |
| 3,293,188 A | 12/1966 | Brown | |
| 3,872,118 A | 3/1975 | Berkowitz | |
| 3,936,385 A | 2/1976 | Cheng | |
| 4,180,467 A * | 12/1979 | Barth | 510/117 |
| 4,229,410 A * | 10/1980 | Kosti | 4/226.1 |
| 4,362,639 A | 12/1982 | Eoga | |
| 4,499,001 A * | 2/1985 | Eoga | 510/100 |
| 4,552,679 A | 11/1985 | Schobel | |
| 5,114,647 A | 5/1992 | Levesque | |
| 5,486,304 A | 1/1996 | Eoga | |
| 5,738,840 A * | 4/1998 | Richter | 424/53 |
| 5,843,406 A * | 12/1998 | Mordarski et al. | 424/49 |
| 6,099,861 A | 8/2000 | DeSenna | |
| 6,491,896 B1 * | 12/2002 | Rajaiah et al. | 424/44 |
| 6,670,312 B2 | 12/2003 | Sugimoto | |
| 6,767,881 B1 * | 7/2004 | Griese et al. | 510/421 |
| 6,815,403 B1 * | 11/2004 | Laney | 510/191 |
| 2003/0059483 A1 * | 3/2003 | Sowle et al. | 424/661 |
| 2004/0115231 A1 * | 6/2004 | Hart et al. | 424/401 |
| 2007/0054830 A1 | 3/2007 | Dullea | |

OTHER PUBLICATIONS

FDA Public Health Notification: Denture Cleanser Allergic Reactions and Misuse, www.fda.gov/cdrh/safety/022508-denturecleansers.html (Feb. 14, 2008).
Gron, P. et al. A Study of Inorganic Constituents in Dental Plaque. J. Dent. Res. Supplement to No. 5, 1969, 48, 799-805.
Kimbrough, R. D. Review of the toxicity of hexachlorophene including its neurotoxicity. J. Clin. Pharmacol. 1973, 13, 439-451.
"Alternative Disinfectants and Oxidants Guidance Manual", United States Environmental Protection Agency, EPA 815-R-99-014, Chapter 4, Apr. 1999.
Thomas, Edwin L., "Myeloperoxidase-Hydrogen Peroxide-Chloride Antimicrobial System: Effect of Exogenous Amines on Antibacterial Action Against *Escherichia coli*", Infection and Immunity, Jul. 1979, vol. 25, No. 1, pp. 110-116.
Hoehn, Robert C., et al., "Considerations for Chlorine Dioxide Treatment of Drinking Water", (Abstract Only) Proceedings of the American Water Works Association Water Quality Technology Conference, Nov. 17-21, 1996, Boston, MA.

* cited by examiner

*Primary Examiner* — Milton I Cano
*Assistant Examiner* — Thuy-Ai Nguyen

(57) ABSTRACT

A novel and safe composition has been discovered that is effective for cleaning dental appliances (e.g. removable braces, retainers, dentures, etc.). This composition bleaches, disinfects, and deodorizes the appliance, while removing plaque that has accumulated on the appliance during wear. The composition comprises a chloramine bleaching agent that liberates hypochlorous acid upon contact with water, a surfactant, a water-soluble carboxylic acid and an alkaline base to produce effervescence and regulate pH, a sequestering agent for alkaline earth metal ions, a drying agent, and an indicator dye that signifies the end of the cleansing process. In a preferred method of using this invention, the premixed components are added to water, and the dental appliance is submerged in the resulting effervescent solution until a color change indicates that cleaning is complete. This invention provides a safe, effective, and convenient method for cleansing and disinfecting dental appliances.

19 Claims, No Drawings

DENTAL APPLIANCE CLEANSING COMPOSITION

CROSS REFERENCE TO RELATED APPLICATIONS

This application claims priority based upon applicants' provisional patent application No. 60/954,942 (filed on Aug. 9, 2007).

FIELD OF THE INVENTION

The present invention pertains to a composition for bleaching, disinfecting, deodorizing, and cleansing dental appliances.

BACKGROUND OF THE INVENTION

The accumulation of residues on dental appliances (e.g., removable braces, retainers, dentures, etc.) is a familiar and persistent problem for wearers of such appliances. These residues often consist of some combination of food particles and biofilm (i.e., plaque), the latter of which is a slime layer that naturally develops when bacteria attach to an inert support. Many of these bacteria produce volatile sulfur compounds as waste products. If the dental appliance is not rid of food particles and biofilm on a regular basis, the malodourous waste products will accumulate, causing the wearer to exhibit bad breath. Even more serious is the potential for pathogenic bacteria to inhabit the biofilm, increasing the likelihood of infection for the wearer. Over time, the biofilm will be converted into dental calculus, which consists of inorganic mineralized salts derived from saliva, bateria, and food particles, as described in U.S. Pat. No. 6,670,312 B2.

In addition to accumulation of residues on the appliance, staining is another widespread problem reported by wearers of dental appliances. Staining of dental appliances is particularly pronounced among coffee and tea drinkers, smokers, and those who use chewing tobacco. Stained dental appliances are unsightly and can be a source of embarrassment for the appliance wearer, sometimes to the extent that the wearer foregoes wearing his or her dental appliance for the sake of vanity.

Although many wearers choose to brush their dental appliance with toothpaste (i.e., mechanical cleaning), others find it more convenient to soak their appliance in a cleansing solution. This cleansing solution is often generated by mixing a commercially available cleansing tablet or powder with water. Though such compositions have achieved considerable popularity and commercial success, there is a continuing need for improvement, especially with respect to plaque removal.

The majority of commercially available effervescent dental appliance cleansing tablets are based on alkaline peroxysalts (e.g., those sold under the tradename Efferdent®), which provide excellent bleaching action but poor plaque removal, as described in U.S. Pat. No. 4,552,679. An additional shortcoming of alkaline peroxysalts is their documented health risk. After seventy-three severe reactions and at least one death, the U.S. Food and Drug Administration issued a statement on Feb. 14, 2008 asking the manufacturers of denture cleansers to revise labeling and to consider appropriate alternatives to persulfate, a common alkaline peroxysalt found in many brands, including Efferdent®. All peroxysalts share a common mode of operation (i.e., liberation of hydrogen peroxide upon contact with water) and a similar structural feature (i.e., an associated molecule of hydrogen peroxide). Therefore, it is an object of the present invention to provide a dental appliance cleansing composition that does not include peroxysalts. Examples of powders and tablets incorporating alkaline peroxysalts can be found in U.S. Pat. Nos. 4,362,639, 4,552,679, and 5,486,304, and U.S. Patent Application 20070054830.

Sequestering agents are necessary to preserve surfactant activity in the presence of calcium and magnesium ions, which are present in dental plaque at 1.5% and 1.0%, respectively, on a dry weight basis [Gron, P., Yao, K., Spinelli, M. A Study of Inorganic Constituents in Dental Plaque. *J. Dent. Res. Supplement to No. 5* 1969, 48, 799-805.] Dental calculus is 30.7% calcium and 1.0% magnesium by weight, according to Encyclopaedia Chimica. Sequestering agents extract alkaline earth metal ions (e.g., calcium and magnesium ions) from the plaque or calculus by forming soluble complexes. This damages the structural integrity of the plaque or calculus, allowing it to be dissolved with the use of surfactants. Furthermore, these agents prevent the complexation of calcium and magnesium ions in the plaque or calculus with the surfactant, which would otherwise lead to surfactant inactivation.

U.S. Pat. No. 5,114,647 to Levesque et al. teaches the preparation of a rapidly dissolving tablet for sanitizing water bodies that consists of an alkali metal cloroisocyanurate bleaching agent admixed with granules of alkali metal carbonate and water-soluble carboxylic acid for effervescence. To enhance cleaning action, the incorporation of a surfactant is also taught. This composition, however, lacks a sequestering agent.

Similarly, in U.S. Pat. No. 6,099,861 to DeSenna et al., a water soluble effervescent tablet formulation is disclosed that contains a bromide releasing agent and a hypochlorite releasing agent. While this tablet offers good disinfecting power over a wide pH range, it also does not contain a sequestering agent for alkaline earth metal ions.

The use of complex phosphates as sequestering agents for alkaline earth metals such as calcium and magnesium in dental plaque is described in U.S. Pat. No. 2,409,718. Though the composition combines the bleaching power of a peroxysalt with a sequestering agent to facilitate plaque removal, it is also known to require 2,2'-dihydroxy-3,5,6,3',5',6'-hexachlorodiphenylmethane(hexachlorophene), a disinfectant, to achieve these cleaning properties. Hexachlorophene has recently been shown to be toxic in neonates [Kimbrough, R. D. Review of the toxicity of hexachlorophene, including its neurotoxicity. *J. Clin. Pharmacol.* 1973, 13, 439-451.], and its use has been limited. The patent teaches that this component is unique and that no alternatives are known. Furthermore, the composition requires the use of a peroxysalt.

U.S. Pat. No. 6,670,312 B2 to Sugimoto et al. teaches the removal of dental calculus using a hydroxycarboxylic acid and sulfamic acid. These agents act very slowly, requiring 24 hours to remove a scale deposit of calcium and magnesium. In addition, the agents are not known to demonstrate bleaching activity.

U.S. Pat. No. 3,293,188 to Brown et al. teaches the preparation of a sterilizing and disinfecting powder consisting of a dichlorocyanurate with "a synergistic carrier agent mixture" of sodium tripolyphosphate and sodium sulfate decahydrate. The high temperature required to prepare this mixture and the presence of water causes significant decomposition of the dichlorocyanurate, however, which results in a corresponding decrease in the available chlorine content of the product, as described in U.S. Pat. No. 3,872,118. Consequently, the low concentration of available chlorine (75 ppm) generated upon dissolution of this powder in water is insufficient for dental appliance bleaching, and the composition is not known to have any plaque removal properties.

U.S. Pat. No. 3,936,385 to Cheng teaches the preparation of an effervescent denture cleanser composition consisting of a chlorine compound which liberates hypochlorite chlorine on contact with water, and a peroxysalt. The pH of the composition dissolved in water must be at least 9. At pH 9 and above, the free chlorine generated upon dissolution of the composition exists almost entirely (>95%) as the hypochlorite anion (OCl$^-$), with a balance of hypochlorous acid (HOCl). According to U.S. Pat. No. 6,099,861, the hypochlorous acid form is known to be the antimicrobial form, while the hypochlorite form exhibits only modest antimicrobial properties. The lower antimicrobial activity of hypochlorite is attributed to its negative charge, which is believed to inhibit its diffusion through the cell wall of microorganisms.

U.S. Pat. No. 3,936,385 also discloses the use of oxidizable dyes in an effervescent denture cleansing composition. Upon contact of the formula with water, these dyes slowly react with the bleaching agent, which causes the solution to change color. Eventually the cleansing solution loses its color completely. This system serves as a time lapse indictor and signals to the user the appropriate time to remove the dental appliance from the cleansing solution.

There remains a need for a safe and convenient composition that is effective for bleaching, disinfecting, deodorizing, and removing plaque and other residues from a wide variety of dental appliances.

BRIEF SUMMARY OF THE INVENTION

The present invention relates to a dental appliance cleansing composition suitable for cleaning removable dental appliances.

It is an object of the present invention to provide an effective composition for bleaching, disinfecting, and deodorizing dental appliances, that does not contain a peroxysalt nor hexachlorophene.

It is another object of the present invention to provide a means of removing dental plaque and calculus from dental appliances.

It is a further object of the present invention to make dental appliance cleaning convenient and pleasant for the user.

It is yet another object of the present invention to provide a composition that can be tailored so that it provides different cleaning strengths.

It is a final object of the present invention to provide a storage-stable composition that is not particularly susceptible to atmospheric moisture.

DETAILED DESCRIPTION OF THE INVENTION

The current invention discloses a dental appliance cleansing composition comprising: a chloramine bleaching agent that liberates hypochlorous acid upon contact with water, a surfactant, a water-soluble carboxylic acid and an alkaline base to produce effervescence and regulate pH, a sequestering agent for alkaline earth metal ions, a drying agent, and an indicator dye that signifies the end of the cleansing process. Optionally employed are a fragrant substance to mask any chlorine odor when the composition is dissolved in water, a binder for allowing the components to be pressed into tablets, and a lubricant to facilitate ejection of the tablets from a die. In a preferred method of using this invention, the premixed components are added to water, and the dental appliance is submerged in the resulting effervescent solution until a color change indicates that cleaning is complete The "chloramine bleaching agent" contained within the composition of the invention is any chemical compound containing one or more chlorine-nitrogen bonds that liberates hypochlorous acid upon contact with water. This hypochlorous acid is in equilibrium with its deprotonated form, hypochlorite, and the equilibrium may be shifted by controlling the pH; below a pH of about 7.5, hypochlorous acid is the predominant form, while above a pH of about 7.5, hypochlorite is the predominant form. Examples of chloramine bleaching agents include, but are not limited to, sodium dicloroisocyanurate (a.k.a. dichloro-s-triazinetrione and triclosene) and sodium trichloroisocyanurate (a.k.a. trichloro-s-triazinetrione and symclosene), and include both the salt and acid forms. Other chloramine bleaching agents are well known in the art and are equally suitable. Without introducing any limitations to the scope of this invention, it should be noted that the salts have higher water solubility than the corresponding acid forms, and are therefore more convenient for use in the present invention. As it relates to this invention, effective dental appliance cleansing compositions are preferably comprised of about 1% to about 20% by weight of one or more chloramine bleaching agents, and more preferably comprised of about 2% to about 10% by weight of one or more chloramine bleaching agents.

The "surfactant" contained within the composition of the invention is any organic compound that contains at least one hydrophobic functional group and one hydrophilic functional group (i.e., an amphiphilic compound). The surfactants may be ionic or non-ionic in nature. Examples of surfactants include, but are not limited to, sodium dodecylsulfate, sodium laureth sulfate, sodium dodecylbenzenesulfonate, alkyl poly (ethylene oxide), and cetyl alcohol. Other surfactants are well known in the art and are equally suitable. As it relates to this invention, effective dental appliance cleansing compositions are preferably comprised of about 0.1 to about 10% by weight of one or more surfactants, and more preferably comprised of about 2% to about 5% by weight of one or more surfactants.

The "water-soluble carboxylic acid" contained within the composition of the invention is any compound containing one or more carboxylic acid functional groups (—COOH) and a solubility in water greater than about 20 g/L. Examples of suitable carboxylic acids include, but are not limited to, oxalic acid, malonic acid, malic acid, maleic acid, and citric acid. Other water-soluble carboxylic acids are well known in the art and are equally suitable. Without introducing any limitations to the scope of this invention, it should be noted that anhydrous forms of the carboxylic acid are preferred to eliminate the possibility of a water of hydration reacting with other components of the formula. As it relates to this invention, effective dental appliance cleansing compositions are preferably comprised of about 5% to about 60% by weight of one or more water-soluble carboxylic acids, and more preferably comprised of about 20% to about 40% by weight of one or more water-soluble carboxylic acids. The water-soluble carboxylic acid is employed at a concentration such that the number of carboxylic acid equivalents exceeds the number of hydroxide equivalents in the alkaline base to ensure that the dental appliance cleansing solution tends toward an acidic pH.

The "alkaline base" contained within the composition of the invention is the basic salt of any alkali metal or alkaline earth metal. Examples of suitable alkaline bases include, but are not limited to, sodium carbonate, sodium bicarbonate, sodium hydroxide, potassium carbonate, potassium bicarbonate, potassium hydroxide, calcium carbonate, and magnesium hydroxide. Other alkaline bases are well known in the art and are equally suitable. It should be noted that the alkaline base need not be soluble in water.

Without introducing any limitations to the scope of this invention, it should also be noted that the alkaline bases formed from an alkali metal (e.g., sodium carbonate) are preferred over the alkaline bases formed from an alkaline earth metal because the latter has a tendency to bind to the sequestering agent. This can be remedied, however, by using an excess of the sequestering agent when the basic salt of an alkaline earth metal is employed. It should be further noted that carbonates and bicarbonates are preferred over hydroxides because latter does not produce effervescence upon reaction with the water-soluble carboxylic acid. As it relates to this invention, effective dental appliance cleansing compositions are preferably comprised of about 5% to about 40% by weight of one or more alkaline bases, and more preferably comprised of about 10% to about 30% by weight of one or more alkaline bases.

The "sequestering agent" contained within the composition of the invention is any compound that binds to alkaline earth metal ions, especially calcium and magnesium, and forms a complex that exhibits some degree of water solubility. Without introducing any limitations to the scope of this invention, it should be noted that condensed phosphates are preferred as sequestering agents. Examples of suitable sequestering agents include, but are not limited to, tetrasodium pyrophosphate ($Na_4P_2O_7$), sodium tripolyphosphate ($Na_5P_3O_{10}$), sodium tetraphosphate ($Na_6P_4O_{13}$), sodium hexametaphosphate (($NaPO_3)_6$), ethylenediaminetetraacetic acid (EDTA), and ethylene glycol tetraacetic acid (EOTA). Other sequestering agents are well known in the art and are equally suitable. It is well known in the art that tetrasodium pyrophosphate preferentially binds magnesium ions, while sodium hexametaphosphate preferentially binds calcium ions. Sodium tripolyphosphate binds to both with good affinity. Without introducing any limitations to the scope of this invention, it should be noted that dental plaque and calculus contain both calcium and magnesium ions, and therefore, a sequestering agent or plurality of sequestering agents that can bind to both ions is preferred. As it relates to this invention, effective dental appliance cleansing compositions are preferably comprised of about 1% to about 20% by weight of one or more sequestering agents, and more preferably comprised of about 5% to about 15% by weight of one or more sequestering agents.

The "drying agent" contained within the composition of the invention is any agent that has the ability to react with, absorb, or adsorb either liquid water or water vapor. Drying agents are also commonly referred to as "desiccants" in the art. Examples of suitable drying agents include, but are not limited to, sodium sulfate, magnesium sulfate, and silica gel. Other drying agents are well known in the art and are equally suitable. Without introducing any limitations to the scope of this invention, it should be noted that drying agents derived from the alkali metals (e.g., sodium sulfate) are preferred over drying agents derived from the alkaline earth metals (e.g., magnesium sulfate) because the latter has a tendency to bind to the sequestering agent. This can be remedied, however, by using an excess of the sequestering agent when a drying agent derived from an alkaline earth metal is employed. As it relates to this invention, effective dental appliance cleansing compositions are preferably comprised of about 10% to about 50% by weight of one or more drying agents, and more preferably comprised of about 20% to about 40% by weight of one or more drying agents.

The "indicator dye" contained within the composition of the invention is any compound that exhibits a colorimetric response when exposed to a solution of the chloramine bleaching agent. This calorimetric response may include, but is not limited to, the change from one color to another, or the disappearance of a color. It should be noted that when a tablet form of the dental appliance cleansing composition described herein is practiced, even dyes that bleach rapidly in the presence of hypochlorous acid may be employed; in this case, the solution color is maintained until the tablet completely dissolves because dye is continually released into the cleansing solution and the tablet affords protection to the dye located in the interior of the tablet. Suitable indicator dyes include, but are not limited to, FD&C Blue No. 1, FD&C Blue No. 2, FD&C Green No. 3, FD&C Red No. 40, FD&C Red No. 3, FD&C Yellow No. 5, FD&C Yellow No. 6. Other indicator dyes are well known in the art and are equally suitable. As it relates to this invention, effective dental appliance cleansing compositions are preferably comprised of about 0.01% to about 1% by weight of one or more indicator dyes, and more preferably comprised of about 0.1% to about 0.2% by weight of one or more indicator dyes.

Optional components may be added to the dental cleansing composition to facilitate its storage and handling, and to make it more pleasing to the user. These optional components include, but are not limited to, a fragrant substance, a tablet binder, and a lubricant.

The "fragrant substance" contained within the composition of the invention is any substance that imparts a pleasant odor to the dental appliance cleansing formula. The fragrance may be used to mask any chlorine odor originating from the dental appliance cleansing formula. Suitable fragrances include, but are not limited to, essential oils, such as peppermint oil, and any other natural or synthetic fragrance. As it relates to this invention, effective dental appliance cleansing compositions are preferably comprised of about 0.1% to about 3% by weight of one or more fragrances, and more preferably comprised of about 0.5% to 1% by weight of one or more fragrances.

The "tablet binder" contained within the composition of the invention is any substance that can be mixed with the other components of the dental appliance cleansing formula and pressed into a tablet form. Suitable binding substances include, but are not limited to, citric acid, polyvinylpyrrolidone, lactose powder, sucrose powder, tapioca starch (cassava flour), and cellulose. Without introducing any limitation to the scope of this invention, it should be noted that citric acid is preferred because it can serve as both the water-soluble carboxylic acid and the tablet binder when it is incorporated in an amount that is preferred for the water-soluble carboxylic acid. The binding substance is not necessary if the dental appliance cleansing composition is practiced in powder form. When employed, the tablet binder is preferably present at about 0.1% to about 10% by weight, and more preferably present at about 0.2% to about 3% by weight.

The "lubricant" contained within the composition of the invention is any substance that can be mixed with the other components of the dental appliance cleansing formula prior to tablet pressing in order to facilitate ejection of the tablet from the die. Suitable lubricants include, but are not limited to, magnesium stearate, stearic acid, magnesium lauryl sulfate, and sodium lauryl sulfate. Without introducing any limitation to the scope of this invention, it should be noted that water-soluble lubricants (e.g., sodium lauryl sulfate, magnesium lauryl sulfate) are preferable to ensure complete dissolution of the tablet. Water-soluble lubricants derived from alkali metals (e.g., sodium lauryl sulfate) are most preferable because the alkali metal ion does not interact with the sequestering agent. Sodium lauryl sulfate (a.k.a. sodium dodecyl sulfate) may also serve as both the surfactant and the lubricant when it is incorporated in an amount that is preferred for the surfactant. The lubricant is not necessary if the dental appliance cleansing composition is practiced in powder form. When employed, the lubricant is preferably present at about 0.1% to about 5% by weight, and more preferably present at about 1% to about 3% by weight.

This invention does not employ peroxysalts, which, according to the US Food and Drug Administration, are known to cause allergic reactions and death even with proper use of the cleaning agents that contain them.

The effectiveness of this composition in bleaching, disinfecting, and deodorizing dental appliances may be due to the liberation of hypochlorous acid upon contact of the chloramine bleaching agent with water. When the composition of the present invention is dissolved in water, the resulting solution tends toward an acidic pH (<7) due to the use of an excess of carboxylic acid equivalents. Acidic pHs favor a high concentration of hypochlorous acid relative to hypochlorite ion, and may increase the disinfecting power of the composition. Hypochlorous acid is a powerful oxidizing agent that bleaches stains, kills microbes, and destroys malodorous organic molecules. In the case of malodorous thiol compounds, which contain sulfur, hypochlorous acid can oxidize them to the considerably less odiferous disulfides.

The effectiveness of this composition in removing dental plaque and calculus may be due to the use of one or more sequestering agents that form water-soluble complexes with calcium and magnesium ions present in plaque and calculus. These ions contribute substantially to the structure of plaque and calculus, and by complexing them, the structural integrity of the plaque or calculus is damaged. The surfactant, which would otherwise be inactivated by the uncomplexed calcium and magnesium ions, can then aggregate around and dissolve the organic components of the plaque or calculus. It is likely that the chloramine bleaching agent also facilitates the breaking up of the organic components.

The effervescence may be due to carbon dioxide gas generated by reaction of a carbonate or bicarbonate of the alkali or alkali earth metals, with a water-soluble carboxylic acid.

Changes to the indicator dye color may be due to oxidation by the chloramine bleaching agent.

Effervescence facilitates tablet dissolution and eliminates the need for stirring to dissolve the components, and the incorporation of an indicator dye provides a convenient signal to the user to remove the dental appliance from the cleansing solution.

The inclusion of more than one chlorarnine bleaching agent, surfactant, and/or sequestering agent into the composition may allow for the possibility of generating a higher strength, and therefore faster acting and more effective, composition by having a higher total concentration of chloramine bleaching agent, surfactant, and/or sequestering agent dissolved in solution. This advantage is afforded by a general principle of chemical solubility, in which dissimilar counterions (e.g. carbonate and borate, sodium and potassium, etc.) in the same solution do not appreciably affect the solubility of each other. As an example, a solution could be saturated with both lithium dichloroisocyanurate and sodium trichloroisocyanurate to give a higher concentration of hypochlorous acid than if the solution were saturated with lithium dichloroisocyanurate or sodium trichloroisocyanurate alone.

The drying agent may increase the shelf life of the composition by removing atmospheric moisture before this moisture can interact with water-sensitive components in the composition. It is also believed that the drying agent allows the mixture to be handled in air for several hours without detriment to the efficacy of the composition.

The currently preferred embodiment of the invention is set forth in the following examples. These examples are intended to illustrate the invention and demonstrate its benefits and safety. No limitation on the full scope and spirit of the invention is, however, to be inferred from these examples alone.

Examples 1, 2, and 3 describe the compositions for low strength, medium strength, and high strength formulas, respectively. Examples 4-6 describe various tests carried out using the compositions described in Examples 1 and 3.

EXAMPLE 1

Sodium carbonate (35.0 g), sodium sulfate (60.0 g), anhydrous citric acid (55.0 g), sodium tripolyphosphate (20.0 g), sodium dichloroisocyariurate (6.0 g), FD&C Blue No. 2 (0.258 g), and peppermint oil (1.4 g) were mixed intimately and crushed using a mortar and pestle. Sodium dodecyl sulfate (5.0 g) was gently stirred into the mixture and the tablets were pressed using a TDP-30 benchtop model single-punch tablet press and an 18 mm flat bevel punch die. The final tablet weight was 3.85 g and the thickness was 7.6 mm.

EXAMPLE 2

Sodium carbonate (35.0 g), sodium sulfate (60.0 g), anhydrous citric acid (55.0 g), sodium tripolyphosphate (20.0 g), sodium dichloroisocyanurate (12.0 g), FD&C Blue No. 2 (0.5 g), and peppermint oil (1.4 g) were mixed intimately and crushed using a mortar and pestle. Sodium dodecyl sulfate (5.0 g) was gently stirred into the mixture and the tablets were pressed using a TDP-30 benchtop model single-punch tablet press and an 18 mm flat bevel punch die. The final tablet weight was 3.85 g and the thickness was 7.9 mm.

EXAMPLE 3

Sodium carbonate (35.0 g), sodium sulfate (60.0 g), anhydrous citric acid (55.0 g), sodium tripolyphosphate (20.0 g), sodium dichloroisocyanurate (18.0 g), FD&C Blue No. 2 (0.774 g), and peppermint oil (1.4 g) were mixed intimately and crushed using a mortar and pestle. Sodium dodecyl sulfate (5.0 g) was gently stirred into the mixture and the tablets were pressed using a TDP-30 benchtop model single-punch tablet press and an 18 mm flat bevel punch die. The final tablet weight was 3.85 g and the thickness was 8.6 mm.

EXAMPLE 4

An Invisalign® aligner coated with dental plaque (accumulated during several days of wear without cleaning) was stained using a FD&C Red No.3 plaque disclosing tablet dissolved in water. The dental appliance was rinsed free of non-specifically bound disclosing dye and submerged in a container of water (~100 ml) containing one tablet of the dental appliance cleanser, which was prepared as described in Example 1. Effervescence began immediately and continued for about twenty minutes. During this time, the solution was blue in color. Ten minutes after the tablet completely dissolved and effervescence ceased, the solution became colorless. The aligner was removed from the cup and rinsed thoroughly with water. After cleaning, the aligner was again placed in a solution of the plaque disclosing dye for ten minutes, and then rinsed briefly with water. No staining was observed, which indicated that the dental plaque had been completely removed during the cleaning process. No aftertaste could be detected on the aligner after the cleaning procedure.

EXAMPLE 5

A pristine Invisalign® aligner was stained by submersion in red wine overnight. The dental appliance was briefly rinsed with water and submerged in a container of water (~100 ml) containing one tablet of the dental appliance cleanser, which was prepared as described in Example 1. Effervescence began immediately and continued for about twenty minutes. During this time, the solution was blue in color. Ten minutes after the tablet completely dissolved and effervescence ceased, the solution became colorless. The aligner was removed from the cup and rinsed thoroughly with water. No color could be detected on the aligner, indicating complete bleaching of the red wine stain. In addition, no aftertaste could be detected on the aligner after the cleaning procedure.

EXAMPLE 6

A pristine Invisalign® aligner was submerged in a container of water (~100 ml) containing one tablet of the dental appliance cleanser, which was prepared as described in Example 3. Effervescence began immediately and continued for about twenty minutes. During this time, the solution was blue in color. Ten minutes after the tablet completely dissolved and effervescence ceased, the solution became colorless. The aligner was removed from the cup and rinsed thoroughly with water. A cytotoxicity screening (ISO 10993-5) was performed by Micromed Laboratories on Feb. 7, 2008, which confirmed that no toxic agents leached from the aligner after cleaning; a confluent monolayer of mouse fibroblast cells were successfully cultured on the aligner, of which 0% of cells exhibited intracellular granulation, 0% of cells exhibited lysis, and 0% of cells exhibited rounding.

We claim:

1. A dental appliance cleansing composition, which becomes active upon contact with water, that comprises:
 (a) a chloramine bleaching agent, wherein the chloramine bleaching agent comprises about 1% to about 20% by weight of the composition,
 (b) a surfactant,
 (c) an effervescence system,
 (d) a sequestering agent for alkaline earth metal ions,
 (e) a drying agent, and
 (f) FD&C Blue No. 2, wherein the FD&C Blue No. 2 comprises about 0.01% to about 1% by weight of the composition, wherein the FD&C Blue No. 2 has the characteristic of exhibiting a first colorimetric response prior to reaction with the chloramine bleaching agent, wherein the FD&C Blue No. 2 has the characteristic of exhibiting a second colorimetric response when all of the FD&C Blue No. 2 has reacted with the chloramine bleaching agent, wherein a time period between the first colorimetric response and the second colorimetric response is the time period for exposing the dental appliance to the composition, and does not contain a peroxysalt.

2. A cleansing composition according to claim 1 wherein said chloramine bleaching agent is selected from the group consisting of sodium dicloroisocyanurate and sodium trichloroisocyanurate, and mixtures thereof.

3. A cleansing composition according to claim 1 wherein the surfactant is selected from the group consisting of sodium dodecylsulfate, sodium laureth sulfate, sodium dodecylbenzenesulfonate, alkyl poly(ethylene oxide), and cetyl alcohol, or mixtures thereof.

4. A cleansing composition according to claim 1 wherein the surfactant comprises about 0.1% to about 10% by weight of the composition.

5. A cleansing composition according to claim 1 wherein the effervescence system consists of a water-soluble carboxylic acid and an alkaline base.

6. A cleansing composition according to claim 5 wherein the number of carboxylic acid equivalents exceeds the number of hydroxide equivalents in the alkaline base.

7. A cleansing composition according to claim 5 wherein the water-soluble carboxylic acid is selected from the group consisting of oxalic acid, malonic acid, malic acid, maleic acid, and citric acid, or mixtures thereof.

8. A cleansing composition according to claim 5 wherein the alkaline base is selected from the group consisting of sodium carbonate, sodium bicarbonate, potassium carbonate, and potassium bicarbonate, or mixtures thereof.

9. A cleansing composition according to claim 1 wherein the sequestering agent is a condensed phosphate.

10. A cleansing composition according to claim 9 wherein the sequestering agent is selected from a group consisting of tetrasodium pyrophosphate, sodium tripolyphosphate, sodium tetraphosphate, and sodium hexametaphosphate, or mixtures thereof.

11. A cleansing composition according to claim 1 wherein the drying agent is selected from the group consisting of sodium sulfate, magnesium sulfate, and silica gel, or mixtures thereof.

12. A cleansing composition according to claim 1 wherein the FD&C Blue No. 2 loses its color sometime after the composition is dissolved in water.

13. A cleansing composition according to claim 1 that is delivered in tablet form.

14. A cleansing composition according to claim 1 that is delivered in powder form.

15. A cleansing composition according to claim 1 that can be delivered in a variety of cleaning strengths by varying the relative concentrations of the components.

16. A cleansing composition according to claim 1 that contains a fragrant substance.

17. A cleansing composition according to claim 1 that contains a tablet binder.

18. A cleansing composition according to claim 1 that contains a lubricant.

19. A dental appliance cleansing composition, which becomes active upon contact with water, comprising:
 (a) sodium dichloroisocyanurate, wherein the sodium dichloroisocyanurate comprises about 1% to about 20% by weight of the composition,
 (b) sodium dodecyl sulfate,
 (c) anhydrous citric acid
 (d) sodium carbonate,
 (e) sodium tripolyphosphate (f) anhydrous sodium sulfate, and
(g) FD&C Blue No. 2, wherein the FD&C Blue No. 2 comprises about 0.01 to about 1 by weight of the composition, wherein the FD&C Blue No. 2 has the characteristic of exhibiting a first colorimetric response prior to reaction with the sodium dichloroisocyanurate, wherein the FD&C Blue No. 2 has the characteristic of exhibiting a second colorimetric response when all of the FD&C Blue No. 2 has reacted with the sodium dichloroisocyanurate, wherein a time period between the first colorimetric response and the second colorimetric response is the time period for exposing the dental appliance to the composition.

\* \* \* \* \*